United States Patent [19]

Wessel

[11] 4,170,736
[45] Oct. 9, 1979

[54] MULTI-PHOTON PHOTOIONIZATION TRACE VAPOR DETECTOR

[75] Inventor: John E. Wessel, Manhattan Beach, Calif.

[73] Assignee: The Aerospace Corporation, Los Angeles, Calif.

[21] Appl. No.: 850,937

[22] Filed: Nov. 14, 1977

[51] Int. Cl.² .............................................. H01J 27/00
[52] U.S. Cl. ................................ 250/423 P; 250/281; 250/423 R
[58] Field of Search ..................................... 250/423 P

[56] References Cited

U.S. PATENT DOCUMENTS

| | | | |
|---|---|---|---|
| 3,558,877 | 1/1971 | Pressman | 250/281 |
| 3,937,956 | 2/1976 | Lyon | 250/423 P |
| 4,000,420 | 12/1976 | Harris | 250/423 P |
| 4,023,038 | 5/1977 | Janes et al. | 250/423 P |

OTHER PUBLICATIONS

"Selective Two-Step"—by Laser Radiation by Ambartzumian et al., Applied Optics, vol. 11, No. 2, Feb. 1972, pp. 354–358.

Primary Examiner—Harold A. Dixon
Attorney, Agent, or Firm—Don B. Finkelstein

[57] ABSTRACT

An arrangement for detecting low concentrations of molecular gases. A gaseous sample containing molecules of the gas to be detected is simultaneously subjected to two photon beams which, for example, may be generated by lasers. The wave length of the first photon beam corresponds to the energy separation between the ground electronic state and an excited electronic state of the molecular gas and the second photon beam contains energy in a wave length corresponding to the energy separation between the excited electronic state and the ionization limit of the molecule. Detection of the amount of ionization achieved is a measure of the concentration of the molecular gas in the sample. Simultaneous identification of the particular wave lengths causing the transition of the molecules from the ground energy state to the excited state provides an additional parameter identifying the molecules.

23 Claims, 7 Drawing Figures

MULTI-PHOTON PHOTOIONIZATION TRACE VAPOR DETECTOR

BACKGROUND OF THE INVENTION

1. Field of the Invention

This invention relates to the molecular gas detection art and more particularly to an improved arrangement for detecting low concentrations of molecular gases by multiple photon absorption techniques.

2. Description of the Prior Art

In many applications there is a need for detecting the presence of molecular gases and identifying the particular molecular gas detected. Such applications include, of course, monitoring of the environmental conditions in many industrial and manufacturing operations, monitoring pollutants such as trace carcinogens or the like and similar applications. It is necessary to detect the presence of and identify various molecular gases. Preferably, such detection and identification may be conducted at the particular location since low concentrations of some molecular gases are some of the components of various mixtures of molecular gases or some of the components sample handling and transport. Additionally, trace contaminents of yet other molecular gases may be introduced during sample preparation and handling.

Optical detection methods are particularly attractive because of high sensitivity, immediate response and suitability for operation at the locations desired and of the optical detection methods ultraviolet spectroscopy has heretofore been widely utilized because it provides comparatively high sensitivity and relative freedom from interference caused by the components of ambient air. However, as applied to molecular gases, the ultraviolet spectroscopy method is hampered since the absorption spectra of complex molecules in the gas phase are broad and generally structure, having many rotational and vibrational bands as well as the presence of hot bands in an overlapping configuration. Fluorescence detection is another method which may be utilized in which excited state energy is emitted by the molecular gas following absorption of energy from an irradiating photon beam. However, spectral interference associated with such fluorescence techniques has limited the lower limit of molecular gas concentration which may be detected by this method.

Photo ionization is one technique which has heretofore been considered for such molecular gas detection and identification. However, single photon photo ionization spectra do not provide a ready identification of the particular gas since the ionization potential of many similar but nevertheless different gases is virtually the same.

Therefore, it has long been desired to provide a detection and identification arrangement for molecular gases which may not only be utilized at the various locations where the gases may be present but also provides the unique identification of the particular gas detected.

SUMMARY OF THE INVENTION

Accordingly, it is an object of the present invention to provide an improved arrangement for detecting molecular gases.

It is another object of the present invention to provide an improved arrangement for detecting comparatively low concentrations of molecular gases.

It is yet another object of the present invention to provide an improved arrangement for detecting comparatively low concentrations of molecular gases and uniquely identifying the particular molecular gases detected.

The above and other objects of the present invention are achieved, according to a preferred embodiment by providing a gaseous sample containing molecules of the molecular gas to be detected and identified. The gaseous sample is irradiated by a first photon beam having a first preselected wave length. The first preselected wave length of the first photon beam corresponds to the energy separation between, for example, the ground electronic state and an excited state of the molecular gas and a characteristic of the molecular gas is that the molecules have a photon inducible transition between the ground energy state and the excited state. Therefore, irradiation of the molecular gas by the first photon beam induces transitions of at least some of the molecules of the molecular gas from the ground energy state to the exicited state. Simultaneously, that is, during the duration of the lifetime of the molecules at the excited state, they are subjected to a second photon beam having a second predetermined wave length. The second predetermined wave length corresponds to the energy separation between the excited state and the ionization limit of the molecule. Another characteristic of the molecule is that the transition between the excited state and the ionization limit may be photon induced and thus the molecules are induced by the second photon beam to undergo transitions to at least the ionization limit.

The amount of ionization is detected. The ionization limit is one characteristic which serves to help identify the particular molecule. Another characteristic which tends to further identify the particular molecule is the wave length at which the transitions from the ground electronic state to the excited electronic state occur. Therefore, detection of these two parameters provides an identification of the particular molecule.

For those molecules where the first wave length is different from the second wave length the unique structural arrangement for providing the simultaneous irradiation of the gaseous sample by the two different photon beams as disclosed herein may be utilized.

BRIEF DESCRIPTION OF THE DRAWING

The above and other embodiments of the present invention may be more fully understood from the following detailed description taken together with the accompanying drawings wherein similar reference characters refer to similar elements throughout and in which.

DESCRIPTION OF THE PREFERRED EMBODIMENTS

Figure 1:
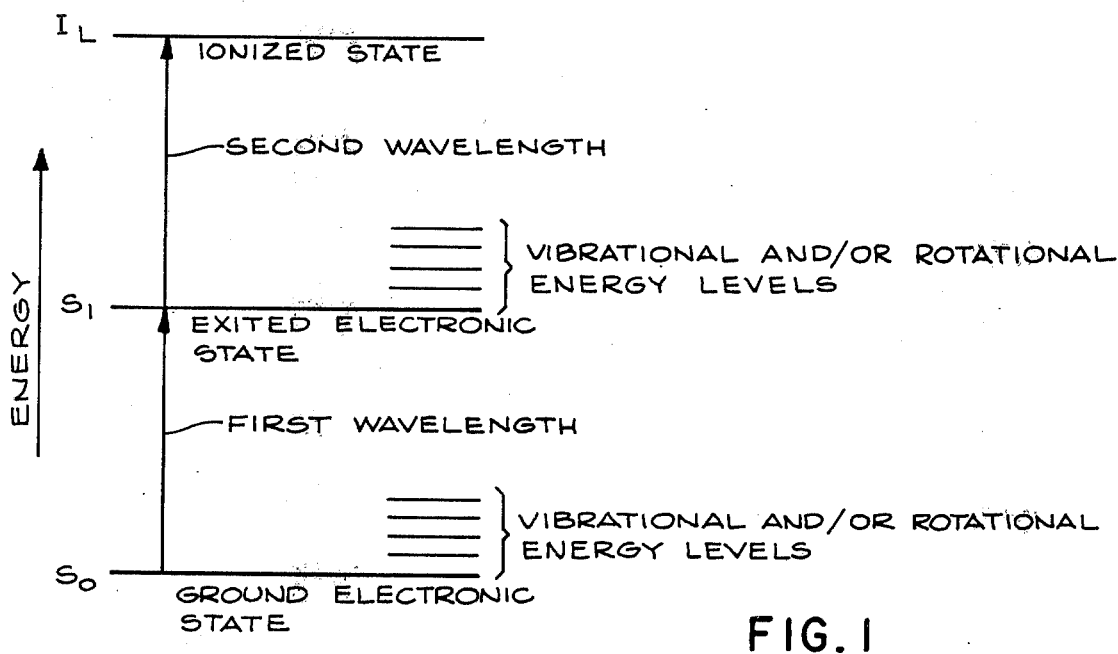
FIGS. 1, 2 and 3 illustrates certain phycial characteristics useful in the practice of the present invention.

Referring now to FIG. 1 of the drawing there is illustrated a generalized energy level diagram for the molecules of a molecular gas of the type to be detected and identified according to the principles of the present invention. $S_0$ represents the ground electronic state and the molecules at the ground electronic state have a plurality of vibrational and/or rotational energy levels. Additionally, there may be other energy levels associated with hot bands or the like. The separation between the vibrational and/or rotational energy levels has been magnified on FIG. 1 for purposes of clarity.

The molecule also has an excited electronic state as indicated at $S_1$. At the excited electronic state there also exists a plurality of vibrational and/or rotational energy levels, hot bands or the like, as indicated on FIG. 1. The energy separation between the ground electronic state and the excited electronic state is indicated by the arrow labeled "first wave length" and the molecules to be detected and identified have photon inducible transitions between the ground electronic state and the excited electronic state. That is, when the molecule is irradiated by a photon having an energy corresponding to the separation between the ground electronic state and the excited electronic state the molecule undergoes a transition to the excited electronic state.

The molecule also has an ionization limit shown on FIG. 1 and $I_L$ and the energy separation between the excited electronic state and the ionization limit is indicated on FIG. 1 by the arrow labeled "second wave length". The molecule also has photon inducible transitions from the excited electronic state to the ionization limit. Thus, when the molecules at the excited electronic state are subjected to photons having energy corresponding to the energy separation between the excited electronic state and the ionization limit, such molecules undergo a transition to the ionization limit.

The ionization limit is generally known for many molecules of the type to be detected and identified. However, many molecules have the same or a very similar ionization limit. Therefore, measurement of the ionization energy, while providing an indication of the identification of a particular molecule, cannot completely identify the molecule because of the similar ionization potentials of other molecules. However the amount of ionization that is achieved is a measure of the concentration of the molecule in the sample subjected to the first and second wave lengths.

Therefore, in order to provide a greater identification of the particular molecule, a second characteristic is measured. This characteristic is the first wave length which induces the transitions of the molecule from the ground electronic state to the excited electronic state. By measuring both the amount of ionization and the ionization limit and also measuring the first wave length at which the transitions of the ground electronic state to the excited electronic state occur, a much more specific identification of the molecule is provided.

Figure 2:
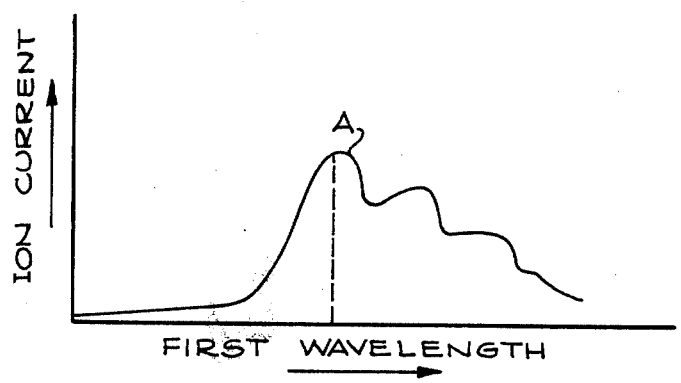

FIG. 2 illustrates the relationship of the amount of ionization by detecting the ion current for a molecular gas subjected to the second wave length as shown on FIG. 1 as the first wave length is varied over a predetermined wave length range. At the point labeled A on FIG. 2 the wave length corresponding to the transition between the ground electronic state and the excited electronic state is achieved. The rather broad spectrum shown on FIG. 2 occurs because of the various energy levels associated with the electronic states of a molecule.

Figure 3:
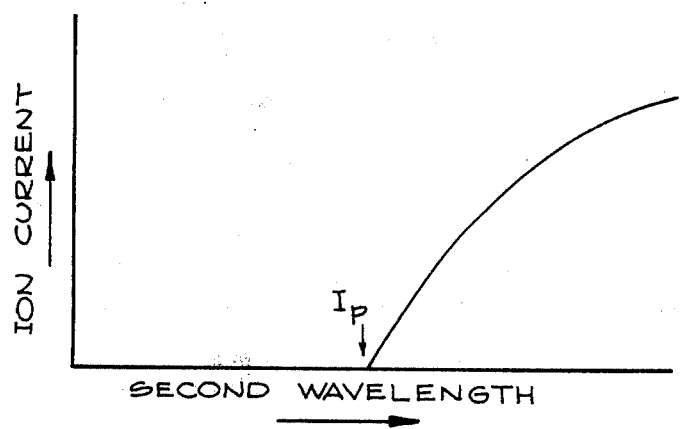

FIG. 3 illustrates the ion current for the condition of the molecular gas subjected to the first wave length as shown on FIG. 1 as the second wave length is varied over a preselected wave length range. No ion current appears until the second wave length achieves the value shown on FIG. 1. At this point the ion current commences to increase as greater number of molecules are pumped up to the ionization potential.

The above description of FIGS. 1, 2 and 3 illustrate the particular characteristics associated with the molecules to be detected and identified according to the principles of the present invention. Thus, knowledge of the ionization limit and the resonance absorption wave length for transitions from the ground electronic state to the excited electronic state now provide a more unique identification of the molecule and measurement of the ion current produced by the ionization provides a measurement of the molecular gas concentration.

For many molecular gases to be detected and identified according to the principles of the present invention the first wave length and the second wave length shown on FIG. 1 are the same or very close in value. In such applications it is possible to utilize a single photon beam to provide both wave lengths. The molecular gas then absorbs photons inducing the transitions to the excited electronic state and this is followed by absorption of photons at the same or a very close wave length to induce transitions to the ionization limit. In such applications, the means for generating the beam of photons having the first and second wave lengths may be, for example, a single laser and the medium may be subjected to a beam from a single laser having this particular wave length. In the preferred embodiments the laser is tunable over the wave lengths associated with the resonance phenomenon.

In other embodiments of the present invention wherein the first wave length is different from the second wave length, two separate lasers are utilized for simultaneously subjecting the gaseous sample containing the molecules to be detected and identified to two separate photon beams, one having photons at the first wave length and the other having photons at the second wave length. By "simultaneously", it will be appreciated, it is meant that while the molecules are in the excited electronic states, they are irradiated by the second photon beam.

Therefore, the present invention contemplates not only the improved method of detection and identification of the molecular gases but also the structural apparatus for achieving such measurement and detection in accordance with the principles of the present invention.

Figure 4:
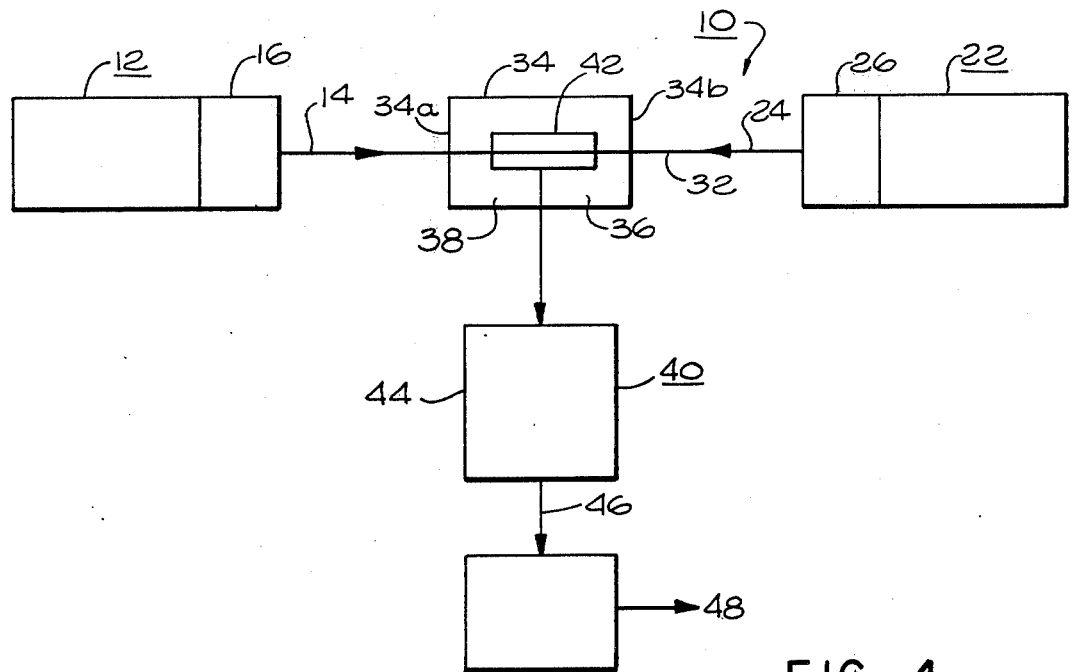
FIG. 4 is a block diagram illustrating a photon beam generating arrangement useful to practice the present invention.

Referring now to FIG. 4 there is illustrated one embodiment, generally designated 10, of the present invention. As shown on FIG. 4 there is provided a first laser 12 for emitting a first beam of photons 14. In preferred embodiments of the present invention the laser 12 is a tunable laser and the wave length of the photons contained within the first photon beam 14 is variable over a predetermined range by the wave length control 16 which also indicates the particular wave length to which the laser 12 is tuned.

A second laser 22 which may be similar to the first laser 12 generates a second photon beam 24 containing photons at the second wave length. The second laser 22 is also preferably a tunable laser which may be tuned by laser control 26 which indicates the particular wave length to which the laser 22 is tuned. As shown on FIG. 4 the first laser 12 and second laser 22 emit their respective photon beams in first directions and along a first axis as illustrated along 32.

A cell 34 may be provided having walls defining a cavity 36 and at least a portion of the walls as indicated at ends 34a and 34b are transparent at least to the first and second wave lengths of the photon beams 14 and 24 respectively and the wave lengths associated with the range over which they may be varied. The gaseous sample containing the molecules of the gas to be detected and identified is indicated at 38 and is contained within the cavity 36.

Detection means, generally designated 40, is provided and comprises an ion current probe 42 positioned within the cavity 36 of the cell 34 for detecting the ion current produced by ionization of the molecular gas 38. Ion current measuring equipment such as amplifiers or the like, of conventional design, are generally indicated at 44 and are provided to generate an information signal 46 having a magnitude proportional to the detected ion current and the information signal 46 may be fed to a display means 48 for display of the measured ion current.

Operation of the embodiment 10 may be conducted in the manner described above in connection with FIGS. 1 and 2. That is, the second laser 22 may be set to emit a second photon beam 24 having the wave length corresponding to the second wave length as illustrated on FIG. 1. The wave length of the first photon beam 14 may then be varied by control 16 over the preselected range which includes the specific first wave length illustrated on FIG. 1 and the ionization current may be measured by the detection means 40. As noted above, the knowledge of the ionization limit of the molecular gas 38 as indicated by the sum of the energies of the first photon beam 14 and second photon beam 24 and the particular wave length associated with the first photon beam 14 provides a more unique identification of the molecular gas 38. Further, the magnitude of the ion current produced in the ion current probe 42 is a measurement of the concentration of the molecular gas 38 within the cavity 36.

It will be appreciated that, in certain circumstances, as noted above, the first wave length may be substantially equal to the second wave length illustrated on FIG. 1. In such embodiments, the second laser 22 may be omitted.

If desired, further operation of the embodiment 10 may be achieved by maintaining the first photon beam 14 at the first wave length illustrated on FIG. 1 and varying the wave length of the second photon beam 24 by means of the laser control 26 over a preselected range to obtain an output as indicated on FIG. 3. Such operation further helps to more specifically identify the particular molecular gas 38.

Increased laser efficiency may be achieved by placing the gaseous sample 38 between the end mirrors of a laser, that is, in the laser cavity where the flux is at the maximum. For the embodiments of the present invention wherein the first wave length is different from the second wave length, the embodiment illustrated in FIG. 5, generally designated 50, has the unique advantage of placing the gas sample between the end mirrors of two separate lasers and in which the gas sample is irradiated along a common axis by both photon beams. As illustrated on FIG. 5 the embodiment 50 comprises a first laser 52 having a laser amplifier 54, a first end mirror 56 and a second end mirror 58. The laser amplifier 54 emits a first photon beam 60 in the first directions and along a first axis. The first photon beam 60 can be adjusted over a wave length range to include photons at a wave length corresponding to the separation between the ground electronic state and the excited electronic state of a particular molecular gas to be detected and identified. Thus, laser 52 may be a tunable laser similar to laser 12 described above.

A second laser 61 which may be similar to the first laser 52 is provided with a laser amplifier 62, a first end mirror 64 and a second end mirror 66 and the laser amplifier 62 emits a second photon beam 68 at the second wave length as illustrated on FIG. 1 corresponding to the energy separation between the excited electronic state and the ionization limit of the particular molecular gas to be detected and identified. A cell 34a which may be similar to the cell 34 shown in FIG. 4 is positioned between the second end mirror 58 of the first laser 52 and the second end mirror 66 of the second laser 61. The particular molecular gas to be detected and identified 38 is contained within the cell 34a. Detection means 40a which may be similar to the detection means 40 described above is also provided. The second end mirror 58 of the first laser 52 reflects the lengths associated with the first photon beam 60 but transmits the wave lengths associated with the second photon beam 68. The second end mirror 66 of the second laser 60 reflects the wave lengths associated with the second photon beam 68 but transmits the photons at the wave lengths associated with the first photon beam 60. Thus, the molecular gas 38 is maintained within the laser cavity of both the first laser 52 and the second laser 61 to increase the efficiency of operation. Operation of the embodiment 50 shown on FIG. 5 may be as described above in connection with the embodiment 10 shown on FIG. 4. Beams 60 and 68 are shown displayed on FIG. 5 for clarity. They may, of course, be colinear.

It will be appreciated that, in the various embodiments of the present invention described herein, the particular wave lengths associated with the first photon beam and second photon beam may be varied by means other than a tunable laser. Such structures may include frequency doubling, or the like.

Figure 6:
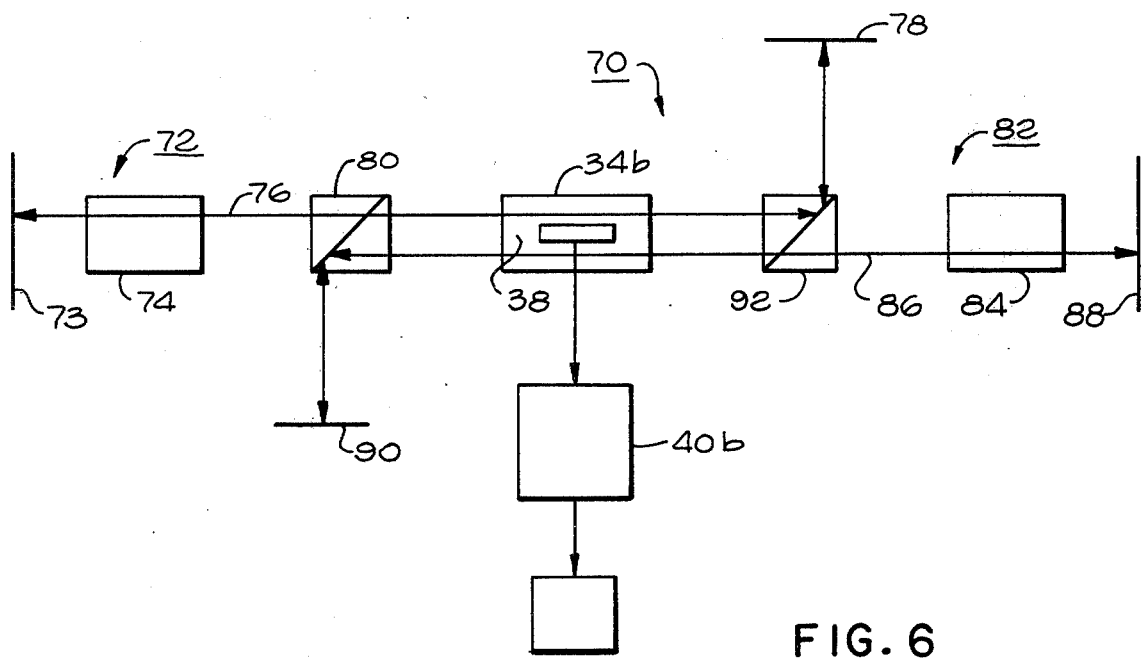
FIG. 6 is a block diagram illustrating another laser arrangement useful in the practice of the present invention.

FIG. 6 illustrates another structural arrangement utilizing two lasers and providing the molecular gas within the laser cavity of both of the lasers. As shown on FIG. 6 the embodiment generally designated 70 comprises a first laser 72 having a laser amplifier 74 which emits a first photon beam 76 containing photons at the first wave length illustrated on FIG. 1 and in a first direction and along a first axis. The first laser 72 has a first end mirror 73 reflecting a photon beam 76 in the first direction and along the first axis, and a second end mirror 78. A first prism polarizer 80 is provided intermediate between the laser amplifier 74 and the second end mirror 78 of the first laser 72 and the first prism polarizer 80 transmits the first photon beam 76 therethrough and imparts a linear polarization thereof for example in the plane of the paper.

A second laser 82 is provided with a laser amplifier 84 which generates a second photon beam 86 having photons at the second wave length shown on FIG. 1 and in the first direction and along or substantially along the first axis. Laser 82 is also provided with a first end mirror 88 and a second end mirror 90. a second prism polarizer 92 is positioned intermedate between the laser cell 84 and the second end mirror 90 and transmits the second photon beam 86 therethrough imparting a second polarization to the second photon beam 86 different from the first polarization, for example, polarization perpendicular to the plane of the paper.

Figure 5:
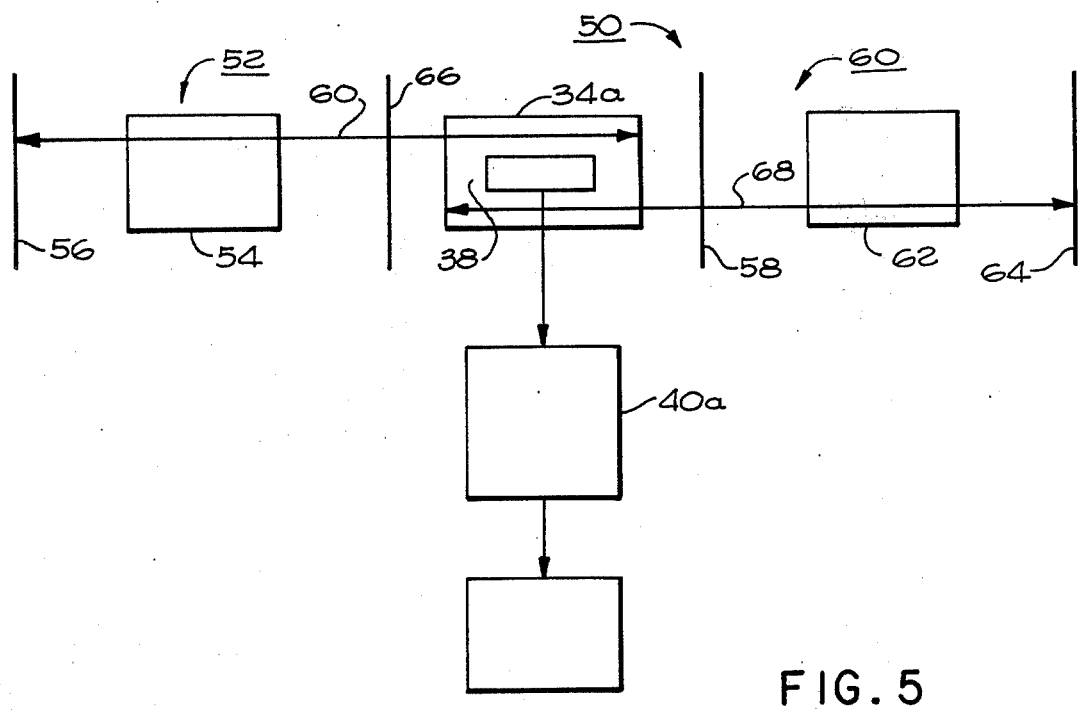
FIG. 5 is a block diagram illustrating a laser arrangement useful in the practice of the present invention.

The second polarizer means 92 acts as a prism for reflecting the photons of the first photon beam 76 and reflects them in a second direction to the second end mirror 78 of the first laser means 72. Similarly, the first prism polarizer 80 acts as a reflector to the second photon beam 86 and reflects the second photon beam 86 in a third direction to the second end mirror 90 of the second laser 82. Depending upon the polarization selected for the second photon beam 86, the second end mirror may be positioned parallel to the plane of the paper and, therefore, reflect the second photon beam in the third direction which is perpendicular to both the first and second directions. The first prism polarizer is oriented to provide this third reflection direction. A cell 34b which may be similar to the cells 34a shown in FIG. 5 and 34 shown in FIG. 4 is provided and contains a molecular gas 38 to be detected and identified. Detection means 40b may also be provided and may be similar to detection means 40a shown in FIG. 5 and 40 shown in FIG. 4. The cell 34b is positioned between the first prism polarizer means 80 and second prism polarizer means 92 and thus is within the laser cavity of both the second laser 82 and first laser 72 to provide increased operational efficiency of the embodiment 70.

Operation of the embodiment 70 may be similar to operation of the embodiment 50 shown in FIG. 5 and 10 shown in FIG. 4.

It has been found that with the techniques of the present invention the molecular gas 38 may be maintained in the cell at one atmosphere pressure thereby allowing for convenient and rapid detection and identification of molecular gases at the particular locations desired.

In some applications of the present invention it may be desirable to utilize a laser arrangement in which mirrors of the type shown in FIG. 5 or prism polarizers of the type shown on FIG. 6 are not utilized but the gas sample is still within the laser cavity of both lasers.

Figure 7:
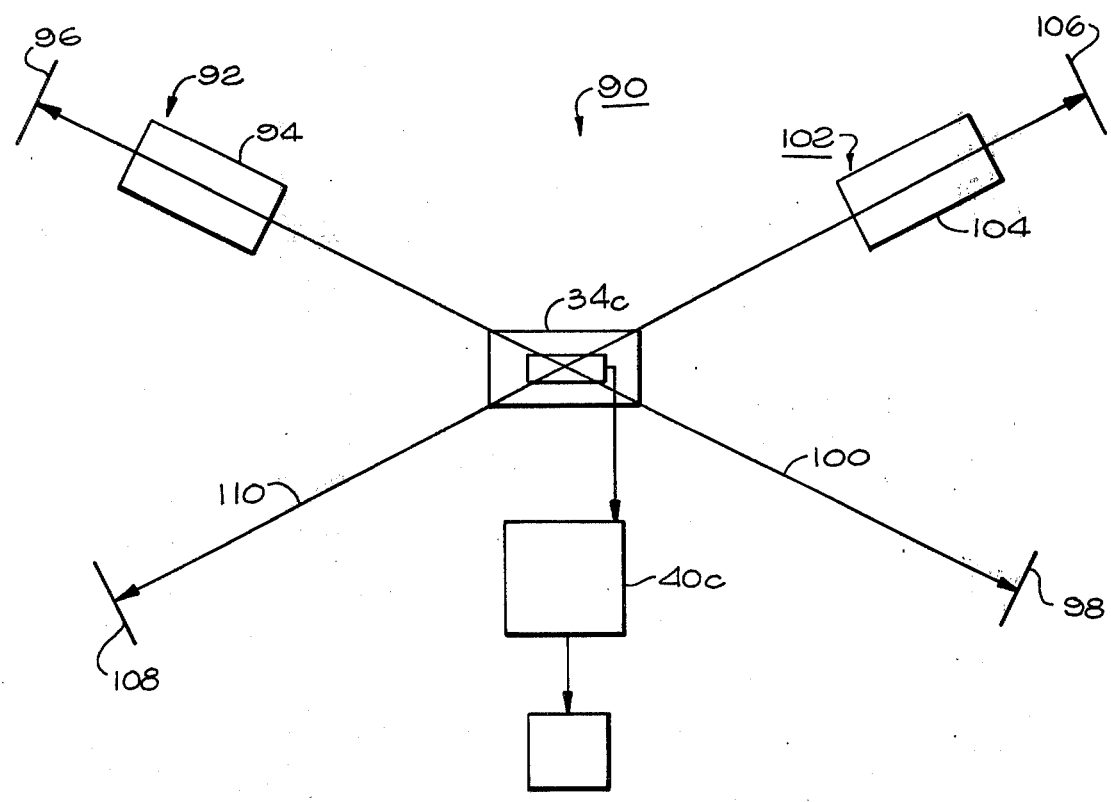
FIG. 7 is a black diagram illustrating another laser arrangement useful in the practice of the present invention.

FIG. 7 illustrates such an embodiment, generally designated 90. A first laser 92 is provided which may be a tunable laser such as laser 12 described above and has a laser amplifier 94, a first end mirror 96 and a second end mirror 98. Lazer 92 generates a first photon beam 100, having photons at a wave length corresponding to the first wave length shown on FIG. 1, in a direction and along a first axis.

A second laser 102 is provided and has a laser amplifier 104, a first end mirror 106 and a second end mirror 108. Lazer 102 generates a second photon beam 110, having photons at a wave length corresponding to the second wave length corresponding to the second wave length shown on FIG. 1, in a second direction and along a second axis different from the first direction and first axis, respectively.

A cell 34c, which may be similar to cells 34, 34a, and 34b described above contains the molecular gas to be identified and is positioned to be irradiated by both photon beams 100 and 110 and is positioned within the laser cavity of each of first laser 92 and second laser 102.

Operation of embodiment 90 may be the same as described above for operation of embodiments 10, 20 and 70.

This concludes the description of the preferred embodiments of this invention. From the above it can be seen that there has been provided an improved method of and apparatus for the detection and identification of molecular gases. Those skilled in the art may find many variations and adaptations of the present invention and the following claims are intended to cover all such variations and adaptations falling within the true scope and spirit thereof.

I claim:

1. A method of detecting and identifying predetermined gaseous molecules wherein the molecules have a plurality of energy states and a predetermined ionized state, and first photon inducible transitions from a first energy state to a second energy state higher than said first energy state, and photon inducible transitions from said second energy state to at least said ionized state, comprising the steps of:

subjecting a gaseous sample containing said predetermined molecules to a first photon beam to induce transitions of at least a portion of said predetermined gaseous molecules from said first energy state to said second energy state;

subjecting said portion of said predetermined gaseous molecules at said second energy state to a second photo beam to induce transitions of at least some of said portion of said predetermined gaseous molucules to said ionized state thereof;

detecting the amount of said ionization; and generating an information signal having a magnitude proportional to said detected amount of ionization.

2. The method defined in claim 1 and further comprising the step of:

maintaining said gaseous sample in a cell at substantially one atmosphere pressure.

3. A method of detecting and identifying predetermined gaseous molecules wherein the molecules have a plurality of energy states and a predetermined ionized state and first photon inducible transitions from a first energy state to a second energy state higher than said first energy state, and photon inducible transitions from said second energy state to at least said ionized state comprising the steps of:

subjecting a gaseous sample containing said predetermined molecules to a first wave length variable photon beam variable over a first predetermined wave length range which includes a first wave length corresponding to the energy difference between said first energy state and said second energy state to cause transitions of at least a portion of said predetermined molecules to said second energy state for the condition of said first photon beam at said first wave length;

subjecting said portion of said predetermined molecules at said second energy state to a second photon beam having energy at a second wave length corresponding to the energy separation between said second energy state and said ionized state of said predetermined molecules to induce transitions to at least said ionized state thereof;

detecting the amount of said ionization; and generating an information signal having a magnitude proportional to said detected amount of ionization.

4. The method defined in claim 3 and further comprising the steps of:

varying the wave length of said first photon beam over said first predetermined wave length range;

recording the wave length of said first photon beam as said first photon beam is varied over said first predetermined wave length range.

5. The method defined in claim 4 and further comprising the step of:
maintaining said gaseous sample in a cell at substantially one atmosphere pressure.

6. A method of detecting and identifying predetermined gaseous molecules wherein the molecules have a plurality of energy states and a predetermined ionized state and first photon inducible transitions from a first energy state to a second energy state higher than said first energy state, and photon inducible transitions from said second energy state to at least said ionized state, comprising the steps of:
subjecting a gaseous sample containing said predetermined molecules to a first photon beam having energy at a first wave length corresponding to the energy difference between said first energy state and said second energy state to cause transitions of at least a portion of said predetermined molecules to said second energy state;
subjecting said portion of said predetermined molecules at said second energy state to a second, variable wave length photon beam variable over a second predetermined wave length range which includes a second wave length corresponding to the energy separation between said second energy state and said ionized state of said predetermined molecules to induce transitions to at least said ionized state thereof for the condition of said second photon beam at said second predetermined wave length;
detecting the amount of said ionization; and
generating an information signal having a magnitude proportional to said detected amount of ionization.

7. The method defined in claim 6 wherein the step of detecting further comprises the step of:
varying the wave length of said second photon beam over said second predetermined wave length range;
recording the wave length of said second photon beam as said second photon beam is varied over said second predetermined wave length range.

8. The method defined in claim 7 wherein the step detecting further comprises the step of:
maintaining said gaseous sample in a cell at substantially one atmosphere pressure.

9. A method of detecting and identifying predetermined gaseous molecules wherein the molecules have a plurality of energy states and a predetermined ionized state, and first photon inducible transitions from a first energy state to a second energy state higher than said first energy state, and photon inducible transitions from said second energy state to at least said ionized state, comprising the steps of:
subjecting a gaseous sample containing said predetermined molecules to a first wave length variable photon beam variable over a first predetermined wave length range which includes a first wave length corresponding to the energy difference between said first energy state and said second energy state to cause transitions of at least a portion of said predetermined molecules to said second energy state for the condition of said first photon beam at said first wave length;
subjecting said portion of said predetermined molecules at said second energy state to a second, variable wave length photon beam variable over a second predetermined wave length range which includes a second wave length corresponding to the energy separation between said second energy state and said ionized state of said predetermined molecules to induce transitions to at least said ionized state thereof for the condition of said second photon beam at said second predetermined wave length;
detecting the amount of said ionization; and
generating an information signal having a magnitude proportional to said detected amount of ionization.

10. The method of claim 9 and further comprising the steps of:
maintaining said second photon beam at said second wave length;
varying the wave length of said first photon beam over said first predetermined wave length range;
recording the wave length of said first photon beam as said first photon beam is varied over said first predetermined wave length range;
varying the wave length of said second photon beam over said second predetermined wave length range;
recording the wave length of said second photon beam as said second photon beam is varied over said second predetermined wave length range.

11. The method of claim 9 and further comprising the step of:
maintaining said gaseous sample in a cell at substantially one atmosphere pressure.

12. An arrangement for detecting and identifying predetermined molecules of the type having a plurality of allowable energy states and a predetermined ionized state and photon inducible transition from a first energy state to a second energy state higher than said first energy state and photon inducible transitions from said second energy state to at least said ionized state comprising, in combination:
a gaseous sample containing said predetermined molecules;
first photon beam generating means for generating a first photon beam at a first wave length corresponding to the energy separation between said first and said second energy states of said predetermined molecule for irradiating said gaseous sample with said first photon beam to induce transitions of at least a portion of said predetermined molecules from said first energy state to said second energy state;
second photon beam generating means for generating a second photon beam having energy at a second wave length corresponding to the energy separation between said second energy state and said ionized state for irradiating said gaseous sample with said second photon beam to induce transitions of at least some of said portion of said molecules at said second energy state to said ionized state thereof; and
first detection means in energy receiving relationship to said gaseous sample for detecting the amount of ionization thereof and generating a first information signal having a magnitude proportional to said detected amount of ionization.

13. The arrangement defined in claim 12 wherein:
said first photon beam generating means is variable to vary the wavelength of said first photon beam over a first predetermined wave length range which includes said first wave length.

14. The arrangement defined in claim 12 wherein:
said second photon beam generating means is variable to vary the wave length of said first photon beam over a second predetermined wavelength range which includes said second wave length.

15. The arrangement defined in claim 12 wherein:
said first wave length is different from said second wave length and said first photon beam generating means comprises a first laser and said second photon beam generating means comprises a second laser.

16. The arrangement defined in claim 15 wherein:
at least one of said first and said second lasers is tunable.

17. The arrangement defined in claim 15 wherein:
said first and said second lasers are tunable.

18. The arrangement defined in claim 15 wherein:
each of said first and said second lasers comprises a first and a second end mirror,
and said gaseous sample is intermediate said first and said second end mirrors of each of said first and said second lasers.

19. The arrangement defined in claim 12 and further comprising:
cell means having walls defining a cavity and said gaseous sample positioned in said cavity, and said walls of said cell means having at least portions thereof substantially transparent to at least said first and said second wave lengths.

20. An arrangement for detecting and identifying predetermined molecules of the type having a plurality of allowable energy states and a predetermined ionized state and photon inducible transitions from said second energy state to at least said ionized state comprising, in combination:
a gaseous sample containing said predetermined molecules;
means for irradiating said gaseous sample with photons having wave lengths corresponding to the energy separation between said first and said second energy states of said predetermined molecule and between said second energy state and said ionized state thereof to induce transitions of at least a portion of said predetermined molecules from said first energy state to said second energy state; and to induce transitions of at least some of said portion of said molecules at said second energy state to said ionized state thereof; and
first detection means in energy receiving relationship to said gaseous sample for detecting the amount of ionization thereof and generating a first information signal having a magnitude proportional to said detected amount of ionization.

21. The arrangement defined in claim 20 wherein:
said first wave length is substantially the same as said second wave length and said means comprises a single laser.

22. An arrangement for irradiating a sample with two photon beams comprising, in combination;
a first laser comprising a first and a second end mirror, and a laser amplifier intermediate said first and said second end mirrors, and said first and said second end mirrors of said first laser reflective of first predetermined wave lengths, and said first laser generating a first photon beam in a first direction along a first axis and said first photon beam having energy in said first predetermined wave lengths;
a second laser means comprising a first and a second end mirror, and a laser amplifier intermediate said first and said second end mirrors, and said first and said second end mirrors reflective of second predetermined wave lengths different from said first predetermined wave lengths for generating a second photon beam in said first direction and substantially along said first axis and said second photon beam having energy in said second predetermined wave lengths;
said second end mirror of said first laser intermediate said laser amplifier of said second laser and said second end mirror of said second laser, and said second end mirror of said first laser substantially transparent to said second predetermined wave lengths; and
said second end mirror of said second laser intermediate said laser amplifier of said first laser and said second end mirror of said first laser, and said second end mirror of said second laser substantially transparent to said first predetermined wave lengths;
whereby said sample to be irradiated is positioned intermediate said second end mirrors of each of said first and second lasers.

23. An arrangement for irradiating a medium with two photon beams comprising, in combination:
a first laser comprising a first laser amplifier for emitting a first photon beam in a first direction along a first axis, and said first photon beam having first wave lengths, a first end mirror for reflecting said first photon beam in said first direction along said first axis, and a second end mirror positioned to reflect said first photon beam in a second direction different from said first direction;
a first prism polarizer means for receiving said first photon beam from said laser amplifier of said first laser and transmitting said first photon beam in said first direction along said first axis and providing a first polarization to said first photon beam;
a second laser comprising a second laser amplifier for emitting a second photon beam having second wave lengths different from said first wave lengths and in said first direction and substantially along said first axis, a first end mirror for receiving said second photon beam and reflecting said second photon beam in said first direction and along said first axis, and a second end mirror positioned to reflect said second photon beam in a third direction different from said first direction;
a second prism polarizer means for receiving said second photon beam from said laser amplifier of said second laser for transmitting said second photon beam in said first direction and along said first axis and providing a second polarization different from said first polarization to said second photon beam;
and said first prism polarizer reflecting said second photon beam in said third direction to said second end mirror of said second laser, and said second prism polarizer means reflecting said first photon beam in said second direction to said second end mirror of said first laser;
whereby said sample to be irradiated is positioned intermediate said first and said second prism polarizer means for irradiation by said first and said second photon beams.

* * * * *